(12) United States Patent
Nakakado et al.

(10) Patent No.: US 7,216,685 B2
(45) Date of Patent: May 15, 2007

(54) METHOD AND APPARATUS FOR PRODUCING WEARING ARTICLE

(75) Inventors: Masaki Nakakado, Osaka (JP); Hitoshi Satoh, Osaka (JP); Satoshi Tanaka, Osaka (JP); Ikuo Tachibana, Osaka (JP)

(73) Assignee: Zuiko Corporation, Osaka (JP)

( * ) Notice: Subject to any disclaimer, the term of this patent is extended or adjusted under 35 U.S.C. 154(b) by 0 days.

(21) Appl. No.: 11/250,849

(22) Filed: Oct. 14, 2005

(65) Prior Publication Data

US 2006/0032589 A1    Feb. 16, 2006

Related U.S. Application Data

(63) Continuation of application No. 10/316,523, filed on Dec. 11, 2002, now Pat. No. 7,008,497.

(30) Foreign Application Priority Data

Aug. 22, 2002  (JP)  ............................ 2002-241959
Oct. 28, 2002  (JP)  ............................ 2002-312403

(51) Int. Cl.
    *B32B 37/00* (2006.01)
(52) U.S. Cl. ...................... 156/494; 156/519; 156/555; 156/582
(58) Field of Classification Search ........ 156/160–164, 156/204–205, 229, 250–256, 494–496, 510, 156/515, 530, 555, 582, 222, 519
    See application file for complete search history.

(56) References Cited

U.S. PATENT DOCUMENTS

| | | |
|---|---|---|
| 3,828,367 A | 8/1974 | Bourgeois |
| 4,425,173 A | 1/1984 | Frick |
| 4,488,923 A | 12/1984 | Pieniak |
| 4,506,779 A | 3/1985 | Seragnoli |
| 4,578,133 A | 3/1986 | Oshefsky et al. |
| 4,610,751 A | 9/1986 | Eschler |
| 4,726,876 A | 2/1988 | Tomsovic, Jr. |
| 4,767,487 A | 8/1988 | Tomsovic, Jr. |
| 4,880,102 A | 11/1989 | Indrebo |

(Continued)

FOREIGN PATENT DOCUMENTS

EP    0 805 116 A1    11/1997

(Continued)

OTHER PUBLICATIONS

European Search Report for corresponding Application No. 01 12 8318 dated Jun. 20, 2002.

*Primary Examiner*—James Sells
(74) *Attorney, Agent, or Firm*—Renner, Otto, Boisselle & Sklar, LLP

(57) ABSTRACT

An apparatus and method for producing a wearing article of the present invention includes supplying an elastic member; stretching the elastic member; placing the stretched elastic member so that the elastic member spreads across a plurality of first webs divided in a transport direction; making a part of a second web loose in the transport direction while transporting the second web, thereby forming a loose portion; placing the first web, on which the elastic member is disposed, on non-loose portion before and after the loose portion of the second web; and cutting the elastic member between adjacent first webs of the plurality of first webs.

25 Claims, 12 Drawing Sheets

U.S. PATENT DOCUMENTS

| | | | |
|---|---|---|---|
| 4,895,568 | A | 1/1990 | Enloe |
| 5,025,910 | A | 6/1991 | Lasure et al. |
| 5,525,175 | A | 6/1996 | Blenke et al. |
| 5,612,118 | A | 3/1997 | Schleinz et al. |
| 5,622,581 | A | 4/1997 | Ducker et al. |
| 5,660,657 | A | 8/1997 | Rajala et al. |
| 5,711,832 | A | 1/1998 | Glaug et al. |
| 6,022,443 | A | 2/2000 | Rajala et al. |
| 6,217,690 | B1 | 4/2001 | Rajala et al. |
| 6,554,815 | B1 | 4/2003 | Umebayashi |
| 6,748,996 | B2 | 6/2004 | Nakakado et al. |
| 2002/0046802 | A1 | 4/2002 | Tachibana et al. |
| 2002/0103468 | A1 | 8/2002 | Nakakado et al. |
| 2002/0125105 | A1 | 9/2002 | Nakakado |

FOREIGN PATENT DOCUMENTS

| | | |
|---|---|---|
| EP | 0 974 323 | 7/1998 |
| GB | 2 214 202 | 8/1989 |
| JP | 1272803 | 10/1989 |
| JP | 63317576 | 12/1998 |
| JP | 2000-026015 | 1/2000 |
| JP | 2001-061890 | 3/2001 |
| WO | 98/00356 | 1/1998 |
| WO | 00/76444 | 12/2000 |

③ Both-end folded state

④ Two-folded state

METHOD AND APPARATUS FOR PRODUCING WEARING ARTICLE

CROSS-REFERENCE TO RELATED APPLICATION

The present application is a continuation of commonly assigned, application Ser. No. 10/316,523, filed Dec. 11, 2002, U.S. Pat. No. 7,008,497 and entitled "Method and Apparatus for Producing Wearing Article", the entire disclosure of which is incorporated herein by reference.

BACKGROUND OF THE INVENTION

1. Field of the Invention

The present invention relates to a method and apparatus for producing a disposable wearing article such as paper diapers and pants.

2. Description of the Related Art

In the above-mentioned type of wearing articles, in order to form, for example, a waist gathering, an elastic member is placed on a sheet surface. However, such an elastic member allows an absorber to shrink, so that the absorber becomes stiff, degrading a feeling of wearing.

As a prior art of cutting an elastic member, Japanese Laid-Open Patent Publication No. 2001-224627 discloses a method for interposing a film sheet for gathering between a peripheral surface of an adsorbent roller and a cutter blade of a cutter roller, and cutting the film sheet.

Furthermore, International publication No. WO 00/04855 discloses a method for forming a web loop.

SUMMARY OF THE INVENTION

In order to achieve the above-mentioned object, a method for producing a wearing article of the present invention includes the steps of: supplying an elastic member; stretching the elastic member; placing the stretched elastic member so that the elastic member spreads across a plurality of first webs divided in a transport direction; making a part of a second web loose in the transport direction while transporting the second web, thereby forming a loose portion; placing the first webs, on which the elastic member is disposed, on non-loose portions before and after the loose portion of the second web; and cutting the elastic member between adjacent first webs of the plurality of first webs.

According to the present invention, the loose portion formed in the second web may be folded into two to form a folded portion. Furthermore, after the first webs are placed, and before and/or after the elastic member is cut, the loose portion of the second web is stretched so as to position the first webs away from each other.

According to the present invention, a method for folding the second web may include the steps of: using a rotation apparatus provided with a plurality of pads which are rotated to continuously transport the second web, thereby supplying the second web to surfaces of the pads with a predetermined interval; allowing the pads to hold the second web on the surfaces of the pads; changing the interval between the adjacent pads supplied with the second web; folding a part of the second web by decreasing the interval between the adjacent pads to make the second web between the adjacent pads loose; and releasing the second web from the pads.

A production apparatus for realizing the production method according to the present invention may includes: a roller for supplying a plurality of first webs divided in a transport direction at a predetermined position in a state where an elastic member is placed so as to spread across the first webs; a rotation apparatus including a plurality of pads which are rotated to continuously transport a second web and approach the roller at the predetermined position; and a cutter for cutting the elastic member. In this apparatus, the respective pads of the rotation apparatus have varying circumferential velocities, the respective pads of the rotation apparatus receive the second web at a receiving position upstream from the predetermined position, and after receiving, an interval between the adjacent pads is decreased while the pads are rotated to the predetermined position, whereby a loose portion is formed in the second web, the first webs are placed to be stacked on a surface of the second web on a basis of the pads at the predetermined position, an interval between the adjacent pads is increased while the respective pads of the rotation apparatus are rotated from the predetermined position to a releasing position downstream from the predetermined position, and the cutter cuts the elastic member in the loose portion while the pads are rotated from the predetermined position to the releasing position.

Another method for folding a web may include the steps of: using a rotation apparatus provided with a plurality of pads which are rotated around a predetermined center axis to continuously transport the web, thereby supplying the web to the surfaces of the pads of the rotation apparatus; rotating the adjacent pads supplied with the web at different velocities to change an interval between the pads, thereby making the web between the pads loose; folding the loose web between the adjacent pads; and releasing the web from the pads.

As the rotation apparatus, for example, a rotation apparatus described in U.S. patent application Ser. No. 09/889,275 may be used. A rotation apparatus disclosed in U.S. Patent Application Publication No. US2002/0103468 may also be used. The disclosures of these are incorporated herein by reference.

According to the present invention, an absorber may be placed between a plurality of first webs with the elastic member cut therebetween. In this case, a shrinking force does not act on an absorber, so that the absorber does not become stiff.

As the elastic member in the present invention, a material containing thread rubber, flat rubber, mesh-shaped rubber, a film, or a thermoplastic elastic member may be adopted. As a material containing a thermoplastic elastic member, hot-melt resin is considered. Furthermore, a plurality of holes or slits may be formed in a film.

According to the present invention, the elastic member may be cut with a light cutter. The light cutter may cut the elastic member by irradiating the elastic member between the plurality of first webs with infrared rays and UV-rays. Furthermore, the elastic member may be cut with an ultrasonic wave.

The wearing article may include products or semi-finished products of a wearing article such as disposable diapers, disposable pants, bandages or the like. The wearing article may further include a single body and a stack of sheets such as fabric, non-woven fabric, a liquid-transparent sheet, or a non-liquid-transparent sheet.

Another production method of the present invention may include the steps of: continuously receiving a stacked web on each pad of a decelerating drum in a state where the web is stretched in a flow direction; after receiving the web, decreasing a circumferential velocity of the respective pads that have received the web so as to make an interval between the respective pads narrow, thereby forming a shrunk portion where the web shrinks between the pads, and holding an edge of the web on the respective pads to keep a state where the held edge is stretched; receiving the web onto a main drum from the decelerating drum in a mixed state where the stretched edge and the shrunk portion are present alternately, and transporting the web while keeping the mixed state; and pressing and heating a part or an entire of the edge by a pressing and heating member on the main drum.

The heat capacity of the stretched edge of the web is small. Therefore, a transport velocity of the web is increased by heating the edge, whereby a transport amount per unit time can be increased. In other words, a heating time for heating the edge can be prolonged in accordance with a ratio at which the edge of the web is stretched. Therefore, even when the transport velocity of the web is large, heat-sealing can be conducted exactly.

These and other advantages of the present invention will become apparent to those skilled in the art upon reading and understanding the following detailed description with reference to the accompanying figures.

DESCRIPTION OF THE PREFERRED EMBODIMENTS

Hereinafter, the present invention will be described by way of illustrative embodiments with reference to the drawings.

Embodiment 1

FIGS. 1 to 5A–B show Embodiment 1.

Figure 1:
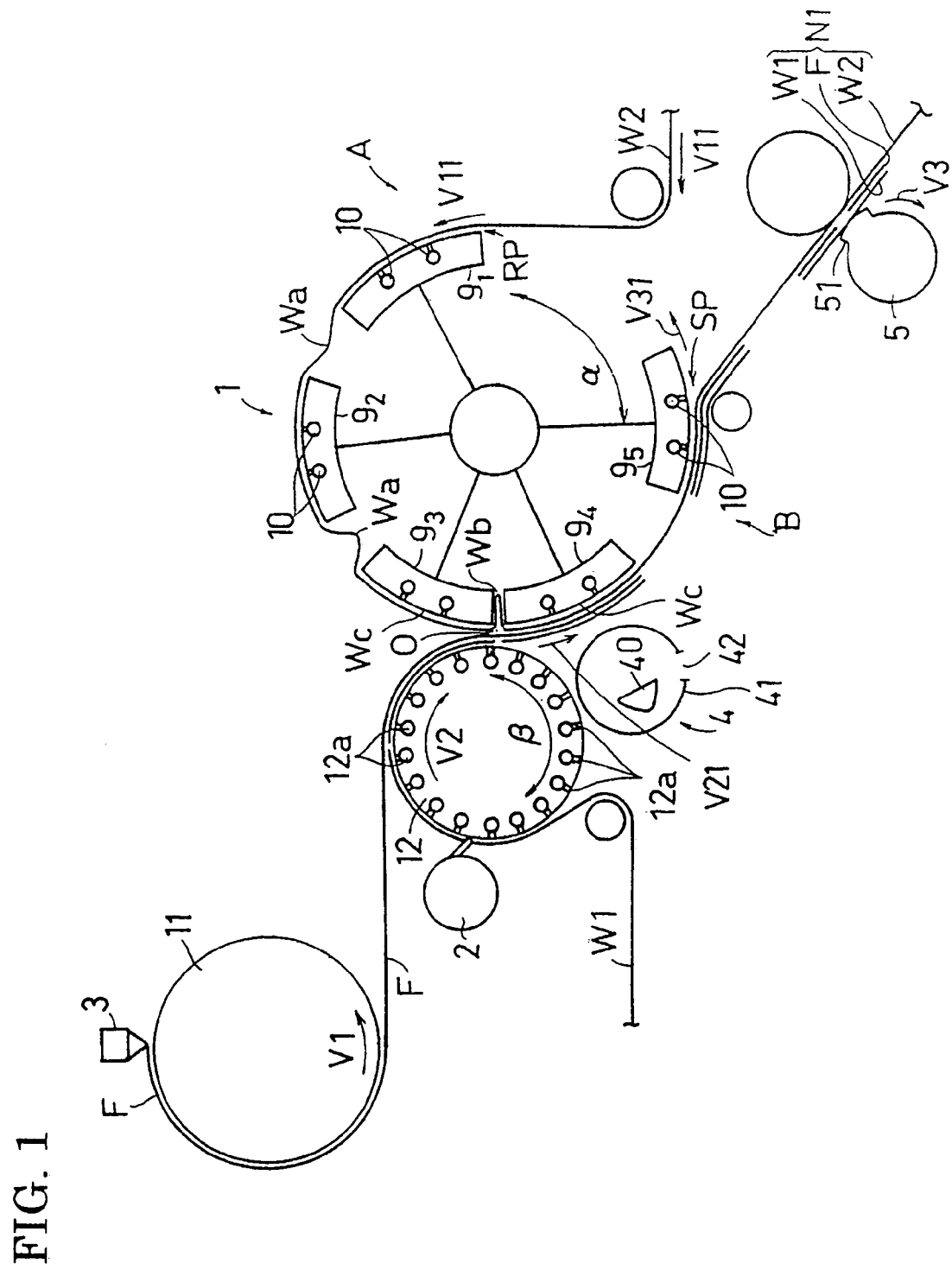
FIG. 1 is a side layout view of an apparatus for producing a wearing article of Embodiment 1 according to the present invention.

An apparatus for producing a wearing article shown in FIG. 1 is capable of providing a web with looseness and intermittently placing an elastic member on at least a part of the web. For example, the apparatus for producing a wearing article includes a rotation apparatus 1 capable of providing a second web W2 with looseness and a second roller 12 capable of placing an elastic member F on portions of the second web W2 other than those which are loose. When the elastic member F extending across a loose portion of the second web W2 is cut with at least one of a laser, an industrial light, a blade, and scissors, the apparatus can intermittently place the elastic member F on the second web W2. This intermittent placement is mainly caused by the looseness of the second web W2. Hereinafter, the configuration and operation of the rotation apparatus 1, the second roller 12, and the like will be described.

In FIG. 1, a supply apparatus 3 of the elastic member F supplies the elastic member F to the surface of a first roller 11. The elastic member F on the first roller 11 is fed to the second roller 12. A circumferential velocity V2 of the second roller 12 is set to be larger than a circumferential velocity V1 of the first roller 11. Therefore, the elastic member F is stretched between the first roller 11 and the second roller 12.

The second roller 12 is supplied with a first web W1. The second roller 12 transports the first web W1 while sucking the first web W1 by vacuum suction or the like. On the surface of the second roller 12, for example, a number of suction holes 12a for sucking the first web W1 may be provided. After the first web W1 is sucked to be held on the surface of the second roller 12 by vacuum suction or the like, the first web W1 is divided into a predetermined size with a web cutter 2. In this division, the first web W1 may be cut or half-cut to a predetermined length in a transport direction. In the case where the first web W1 is half-cut, the first web W1 may be cut to a predetermined length together with the elastic member F in a subsequent step or cut in a predetermined length when an interval of pads is increased. After this division, the elastic member F is placed so as to spread across the surface of the respective first webs W1. In the case where the elastic member F is made of thread rubber or flat rubber, an adhesive is applied to at least one of the elastic member F, the first web W1, and the second web.

It may also be possible that after the elastic member F is placed on the first web W1, the elastic member F is cut together with the first web W1. Furthermore, in the case where the elastic member F is made of hot-melt resin, molten resin discharged from the supply apparatus 3 is cooled by the first roller 11. The molten resin may be cooled with cool water. Furthermore, the first roller 11 may be a porous roller. In the case where the first roller 11 is a porous roller, the first roller 11 may be configured so that air is discharged from the inside of the first roller 11 through holes. Due to the air, the hot-melt resin becomes unlikely to adhere to the roller. When the air is discharged from the porous body, the volume of the air is increased to cool the roller. Thus, the hot-melt resin can be cooled. The porous roller may be formed by sintering stainless ball or the like.

Furthermore, it may also be possible that the first roller 11 is be provided with grooves or the like, whereby resin is molded. For example, mesh-shaped (for example, lattice-shaped) grooves are formed on the first roller 11, and hot-melt resin is applied to the grooves of the first roller 11 with a coater or the like, whereby a mesh-shaped elastic member is formed.

When hot-melt resin having a softening point lower than that of Lycra® is used as the elastic member, the subsequent cutting step becomes easier, compared with the case of using Lycra®.

The rotation apparatus 1 for folding is placed in the vicinity of the second roller 12. The rotation apparatus 1 has a plurality of pads 9 capable of sucking the second web W2 and transporting it. On the surface of a pad $9_i$, suction holes 10 for sucking the second web W2 are provided. The rotation apparatus 1 continuously transports the second web W2, and is in contact with the surface of the second roller 12 via the first web W1, the elastic member F, and the second web W2 at a contact point 0 (predetermined position). Thereafter, the following may also be possible: an additional roller and the pad $9_i$ sandwich the first web W1, the elastic member F, and the second web W2 placed on the pad $9_i$, whereby the contact therebetween is enhanced.

The elastic member F is cut after being interposed between the first web W1 and the second web W2. The elastic member F is fixed between the webs W1 and W2, so that the elastic member F shrinks less, compared with the case where the elastic member F is placed on one web.

Figure 5B:
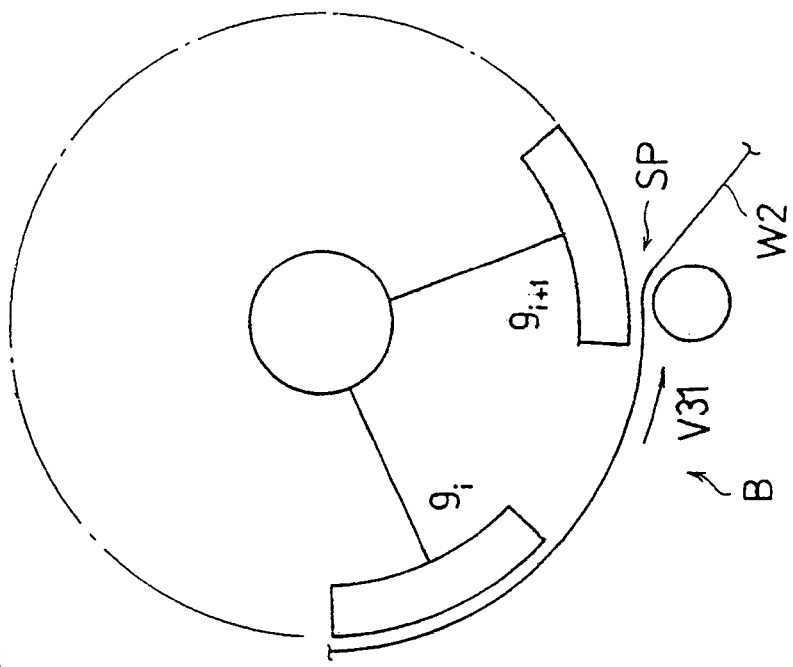
FIGS. 5A and 5B are partial side views showing a circumferential velocity of pads.
Figure 5A:
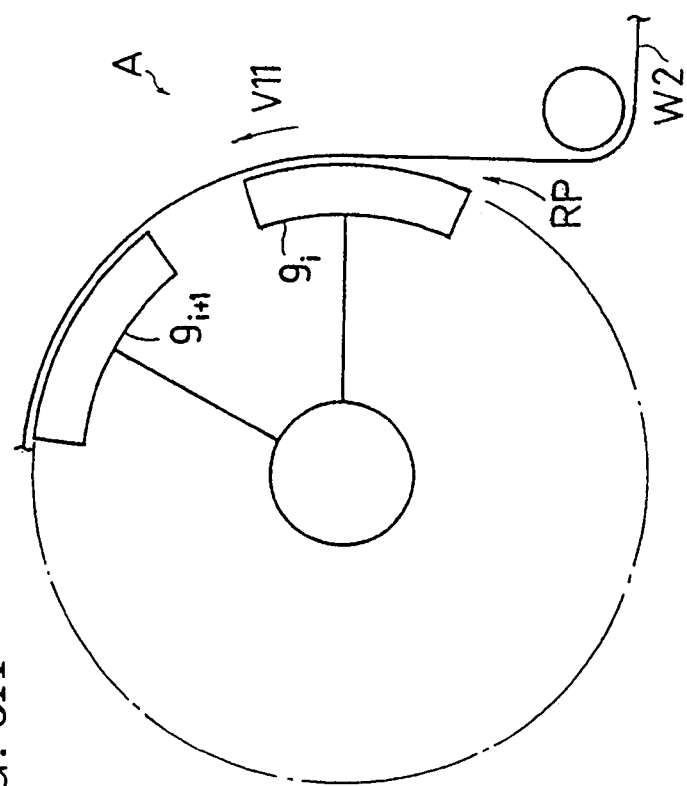

The rotation apparatus 1 receives the second web W2 at a circumferential velocity V11 at a receiving position RP. At a point "A" where the pad $9_i$ receives the second web W2, the circumferential velocity of the pad is V11. FIG. 5A is a side view showing the enlarged vicinity of the point "A" of FIG. 1. During a period from a time when at least a part of the pad $9_{i+1}$ shown in FIG. 5A receives the second web W2 to a time when at least a part of the pad $9_{i+1}$ adjacent to the pad $9_{i+1}$ receives the second web W2, the pad $9_{i+1}$ moves at a substantially constant circumferential velocity V11. The reason for this is to prevent the second web W2 from being damaged.

Each pad $9_i$ of the rotation apparatus 1 is rotated at the receiving position RP at the circumferential velocity V11, and decelerates to a circumferential velocity V21 before reaching the contact point 0 (where the distance between the pad $9_i$ and the pad $9_{i+1}$ becomes minimum). Therefore, the interval between the pad $9_i$ and the pad $9_{i+1}$ becomes narrow before the pad $9_i$ moves from the receiving position RP to the contact point 0. This causes the second web W2 to become loose between the pad $9_i$ and the pad $9_{i+1}$, whereby a loose portion Wa is formed.

The pad $9_i$ comes into contact with the second roller 12 via the second web W2 and the like at the circumferential velocity V21 (V11>V21) at the contact point 0 shown in FIG. 1. The first web W1 is transferred from the second roller 12 at the circumferential velocity V2. The circumferential velocity V21 of the pad $9_i$ is set at a substantially constant velocity equal to or close to the circumferential velocity V2 of the second roller 12. That is, while at least the pad $9_i$ is in contact with the second roller 12 via the second web and the like or at least the pad $9_i$ places the first web W1 on the second web W2, the pad $9_i$ moves at the substantially constant circumferential velocity V21 substantially equal to V2. In other words, during a period from a time when the second web W2 on the pad $9_i$ starts receiving the first web W1 to a time when the second web W2 finishes receiving it, the pad $9_i$ moves the constant circumferential velocity V21 (≈V2). The difference in velocity prevents the first web W1 and the second web W2 from being shifted from each other, and exactly places the first web W1 at a predetermined position of the second web W2.

The circumferential velocity of the pad $9_{i+1}$ becomes V31 at a point B where the pad $9_{i+1}$ releases the second web W2. FIG. 5B is a side view showing the enlarged vicinity of the point B. The pad $9_i$ moves at a substantially constant circumferential velocity V31 at least during a period from a time slightly before the pad $9_{i+1}$ adjacent to the pad $9_i$ releases the second web W2 to a time when the pad $9_i$ releases the second web W2 (FIG. 5B). The reason for this is to minimize the fluctuation in velocity of the released second web W2. For example, in the case where the circumferential velocity of an embossing roller 5 is V3, the circumferential velocity V31 becomes substantially equal to V3.

When or after the circumferential velocity of the pad $9_i$ becomes maximum in the vicinity of the point A in FIG. 5A, the pad $9_i$ receives the second web W2. If the pad $9_i$ receives the second web W2 before the circumferential velocity of the pad $9_i$ becomes maximum, the interval between adjacent pads is increased, which may damage the second web W2. As the operation of the pad $9_i$, the pad $9_i$ may move at a maximum circumferential velocity, for example, during a period from the point B to the point A. In this case, a region from the point B to the point A can be dealt with as one region. That is, in the present embodiment, the circumferential velocity of the pad may become substantially constant at least at two points.

It is preferable that the apparatus is provided with a directing part so that the loose portion Wa in FIG. 1 becomes loose exactly toward the center of the rotation apparatus 1.

The directing part may be, for example, a mechanism for jetting air or a mechanism for pushing the loose portion Wa of the web toward the center of the rotation apparatus 1. Alternatively, the directing part may be a mechanism for sucking the web W toward the center of the rotation apparatus 1 by vacuum suction. In the case where the directing part is a mechanism for jetting air, one or a plurality of directing parts may be provided. Furthermore, in the case where the directing part is a mechanism for pushing the loose portion Wa, one or a plurality of directing parts may be provided. By providing a plurality of directing parts, the loose portion Wa can be bent exactly toward the center of the rotation apparatus 1. In the present embodiment, the loose portion Wa may have a shape dented toward the center of the rotation apparatus 1 due to the weight of the second web W2.

Next, a folding operation will be described. When the second web W2 is sucked to be held on the surface of the pad $9_i$ at the receiving position RP, the second web W2 is transported along the pad $9_i$ of the rotation apparatus 1. When the pad $9_1$ is rotated from the receiving position RP to the contact point 0, the interval between the pads $9_i$ is decreased. Because of this, the loose portion Wa is formed in the second web W2. Furthermore, the loose portion Wa is folded into two to form a folded portion Wb.

The rotation apparatus for conducting the above-mentioned "folding" is not limited to the rotation apparatus 1. For example, an apparatus described in Japanese Patent Application No. 2001-545183 A may be used. The present invention is intended to place an elastic member intermittently on a web. Therefore, the second web W2 is not necessarily folded completely. Furthermore, depending upon the shape of the pad $9_i$, the second web W2 may have a loop shape.

Figure 2:
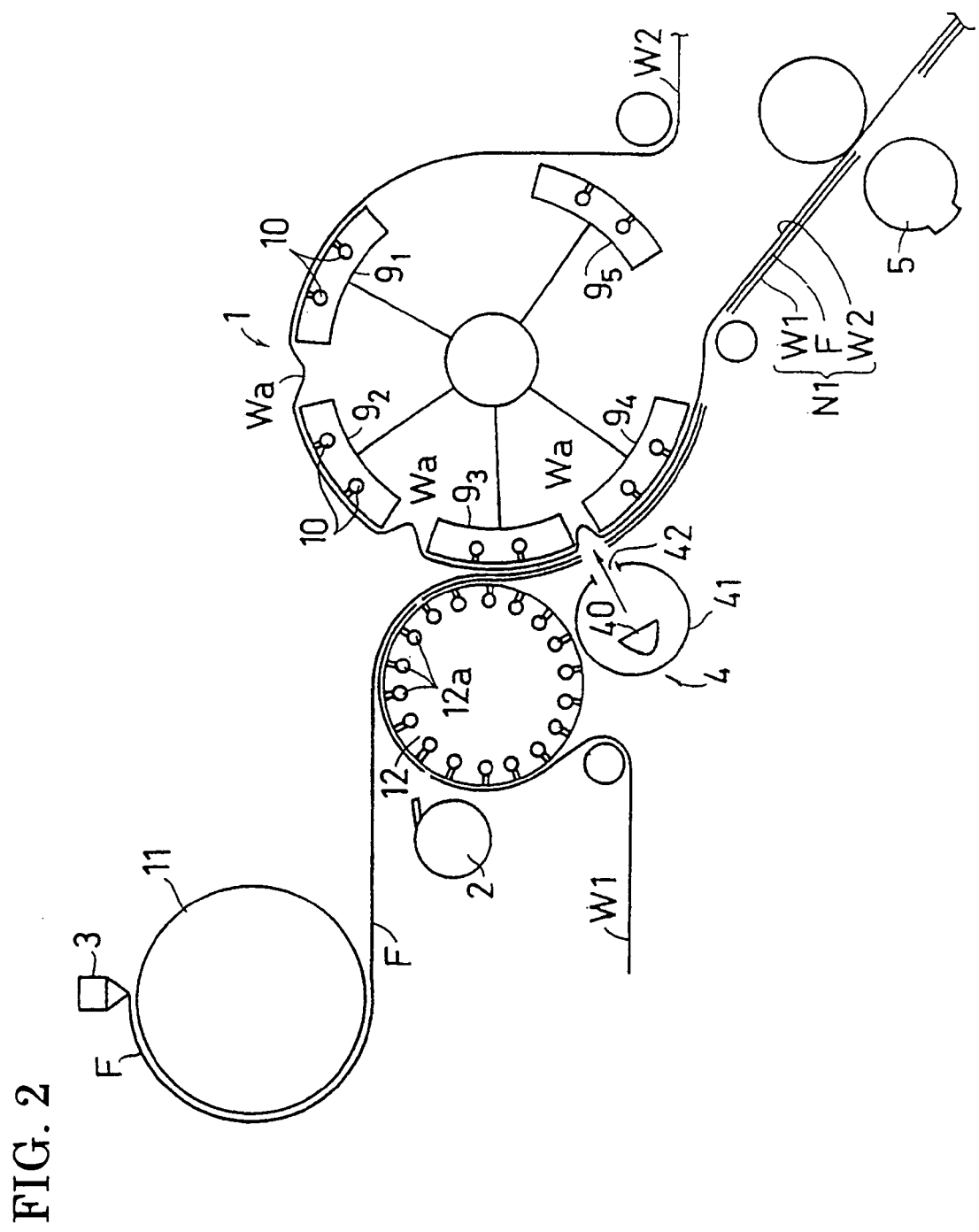
FIG. 2 is a side layout view illustrating the steps of cutting an elastic member in the apparatus shown in FIG. 1.

The folded second web W2 is attached to be stacked on the first web W1 at non-folded portions Wc before and after the folded portion Wb. That is, the elastic member F is not cut until the elastic member F is placed and fixed between the first web W1 and the second web W2. Therefore, the stretched elastic member F hardly shrinks on the second web W2. When the second web W2 is stacked on the first web W1, the first web W1 is not placed on the folded portion Wb folded between the pads $9_i$ and $9_{i+1}$ adjacent to each other in the vicinity of the contact point 0. When the interval between the pads $9_i$ and $9_{i+1}$ is increased as shown in FIG. 2, only the elastic member F is exposed as shown in FIG. 3A.

As shown in FIG. 1, during β from a time when the first web W1 is attached to the second web W2 to a time when the first web W1 is received, suction of air through the suction holes 12*a* of the second roller 12 may be stopped or air may be discharged through the suction holes 12*a*. The purpose of this is to attach the first web W1 to the second web W2 smoothly.

Figure 3A:
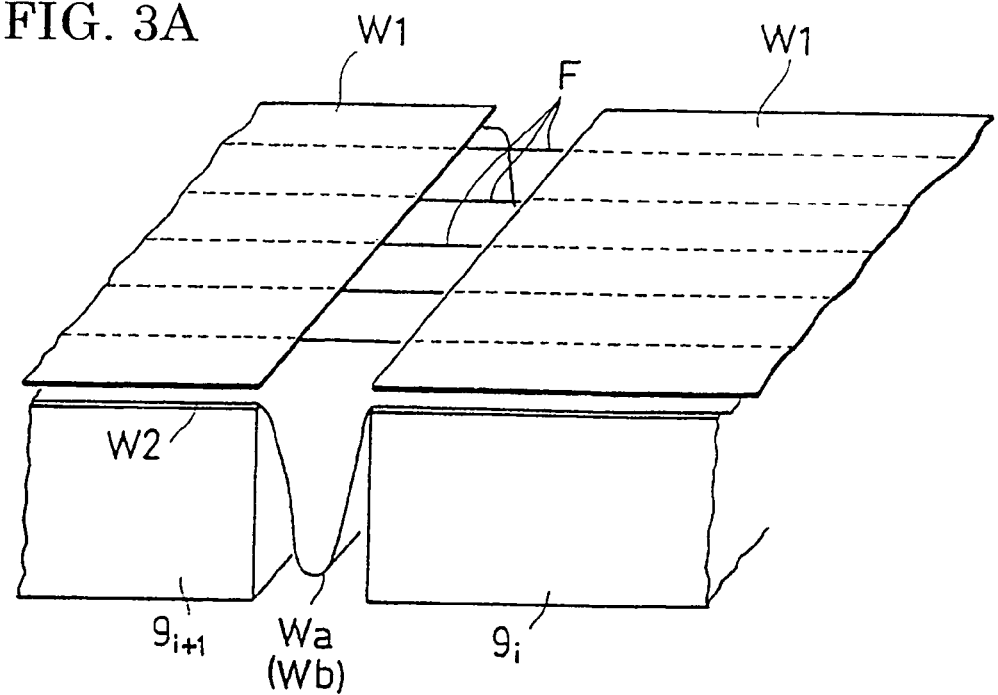
FIG. 3A is a perspective view of a stack in a state before the elastic member is cut.

The exposed elastic member F in FIG. 3A is cut with a cutter. In the case where the elastic member F can be cut with a light cutter, a light cutter 4 shown in FIG. 2 is used. The light cutter 4 has a rotatable cover, and a slit 42 is formed at a part of the cover. The cover 41 with the slit 42 is rotated, whereby infrared rays are radiated intermittently from a light source 40 to the elastic member F to cut it at a predetermined pitch. When the elastic member F is cut with the light cutter 4, there is no possibility that the webs W1 and W2 are damaged by heat from the light cutter 4, since the elastic member F is away from the loose portion Wa. The elastic member F may be cut with a pressure, heat, UV-rays, a laser or at least two of them. Furthermore, the elastic member F may be cut with an ultrasonic wave.

Figure 11A:
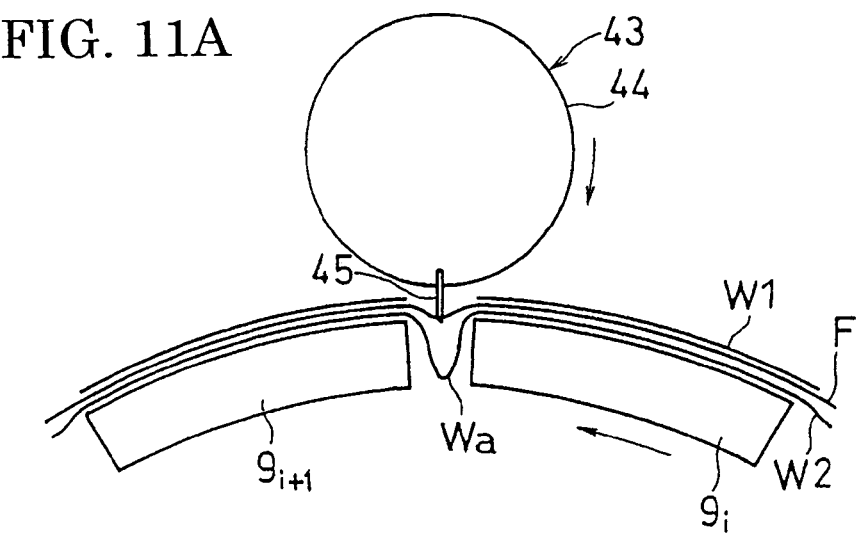
FIGS. 11A to 11C show an example of cutting the elastic member with a cutting machine.
Figure 11B:
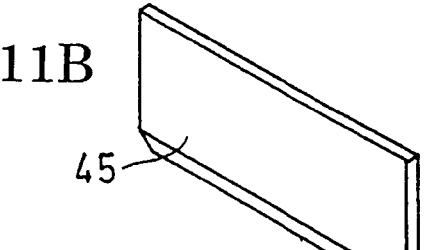
Figure 11C:
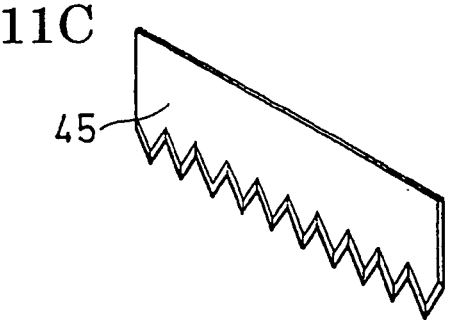

Hereinafter, an example of cutting the elastic member F with a cutter will be described. FIG. 11A is a view showing a cutting machine 43 that is an example of a cutter. The cutting machine 43 has a rotatable roller 44 and a blade 45 placed at the roller 44. The distance between the rotation center of the roller 44 and the center of the rotation apparatus 1 is hardly changed. The blade 45 can cut the elastic member F positioned on the loose portion Wa between the pads $9_i$ and the pad $9_{i+1}$, when the roller 44 is rotated. The rotation of the roller 44 is changed in accordance with the rotation of at least one of the pad $9_i$ and the pad $9_{i+1}$. The blade 45 may have a linear shape (FIG. 11B) or may be in a jagged shape (FIG. 11C). Furthermore, the blade 45 may be reciprocated in the direction of the rotation axis of the roller 4.

Figure 11D:
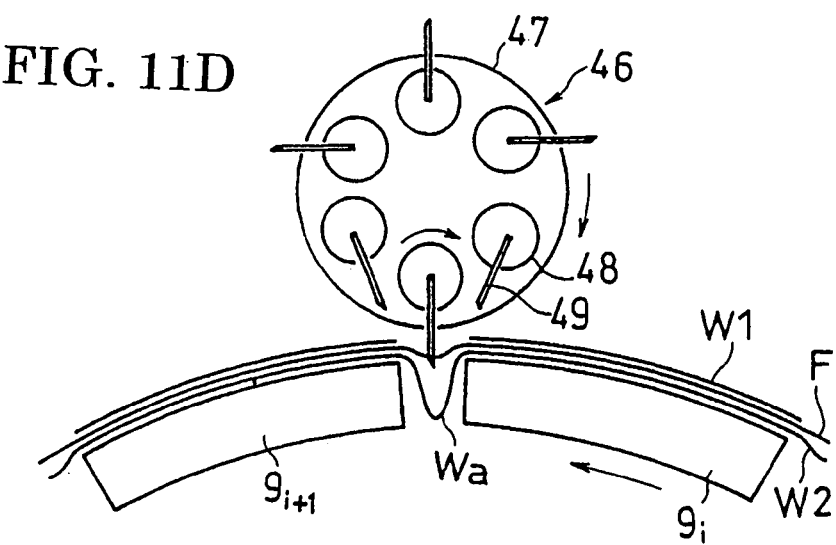
FIG. 11D shows another cutting machine.

FIG. 11D shows another cutting machine 46. The cutting machine 46 includes a rotatable large roller 47, a rotatable small roller 48 attached to the large roller 47, and a blade 49 placed at the small roller 48. The blade 49 of the cutting machine 46 can cut the elastic member F positioned on the loose portion Wa between the pad $9_i$ and the pad $9_{i+1}$, when the large roller 47 and the small roller 48 are rotated. The rotations of the large roller 47 and the small roller 48 are changed in accordance with the rotation of at least one of the pad $9_i$ and the pad $9_{i+1}$. As shown in FIG. 11D, when the blade 49 reaches the bottom dead point, the tip end of the blade 49 is preferably directed to the center of the rotation apparatus 1. Furthermore, in the same way as in the blade 45, the blade 49 may have a shape as shown in FIG. 11B or 11C, and may be reciprocated in the direction of the rotation axis of the large roller 47 or the small roller 48.

The rotation apparatus 1 may be provided with scissors instead of the cutting machine. After the second web W2 is stacked on the first web W1, and the interval between the pad $9_i$ and the pad $9_{i+1}$ is slightly increased, the scissors may enter between the pad $9_i$ and the pad $9_{i+1}$ to cut the elastic member stretched between the pad $9_i$ and the pad $9_{i+1}$. The scissors may enter between the pad $9_i$ and the pad $9_{i+1}$ in accordance with the rotation of at least one of the pad $9_i$ and the pad $9_{i+1}$. In order for the scissors to perform such an operation, at least one of a cam mechanism and a link mechanism may be used.

In FIG. 1, the circumferential velocity of the pad $9_3$ becomes a velocity V31 (V31>V21) at a releasing position SP where the pad $9_3$ releases the second web W2. Therefore, the interval between the pads $9_3$ and $9_4$ is increased from the contact point 0 to the releasing position SP. Therefore, the tension stress and elongation of the elastic member F are increased from the contact point 0 to the releasing position SP. When the elastic member F is cut with the light cutter 4 in this state, cutting becomes easy. At the releasing position SP, a stack N1 in FIG. 3B, in which the webs W1 and W2 and the elastic member F are stacked, is in the state before the folded portion Wb is folded.

Herein, during α from the releasing position SP to the receiving position RP, suction through the suction holes 10 may be stopped, and air may be discharged through the suction holes 10. The purpose of this is to smoothly transfer the stack N1 in a downstream direction.

Figure 3B:
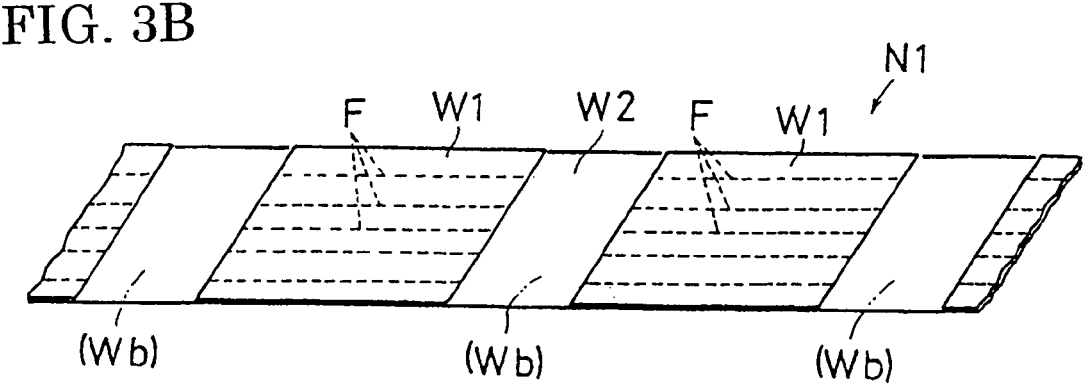
FIG. 3B is a perspective view of a stack in a state after the elastic member is cut.
Figure 4A:
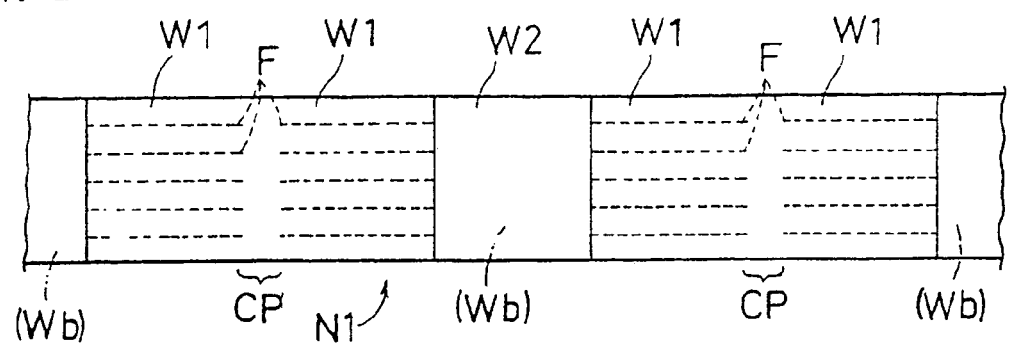
FIG. 4A is a front view showing the stack in which the elastic member interposed between webs is cut.

As shown in FIG. 1, an embossing roller 5 may be provided downstream from the releasing position SP. The stack N1 in FIG. 3B is sent to the embossing roller 5. A plurality of convex portions 51 are arranged on the embossing roller 5, and at least the elastic member F of the stack N1 is cut with the convex portions 51. Because of this, as shown in FIG. 4A, the stack N1 is obtained in which the shrinking force of a part of the elastic member F interposed between the first and second webs W1 and W2 is suppressed. An adhesive is not basically applied to a portion CP where the shrinking force of the elastic member F is suppressed by the embossing roller 5. The reason for this is to protect the shrinking of the elastic member F. However, in order to control the shrinking of the elastic member F, some adhesive weaker than usual may be applied.

Figure 4B:
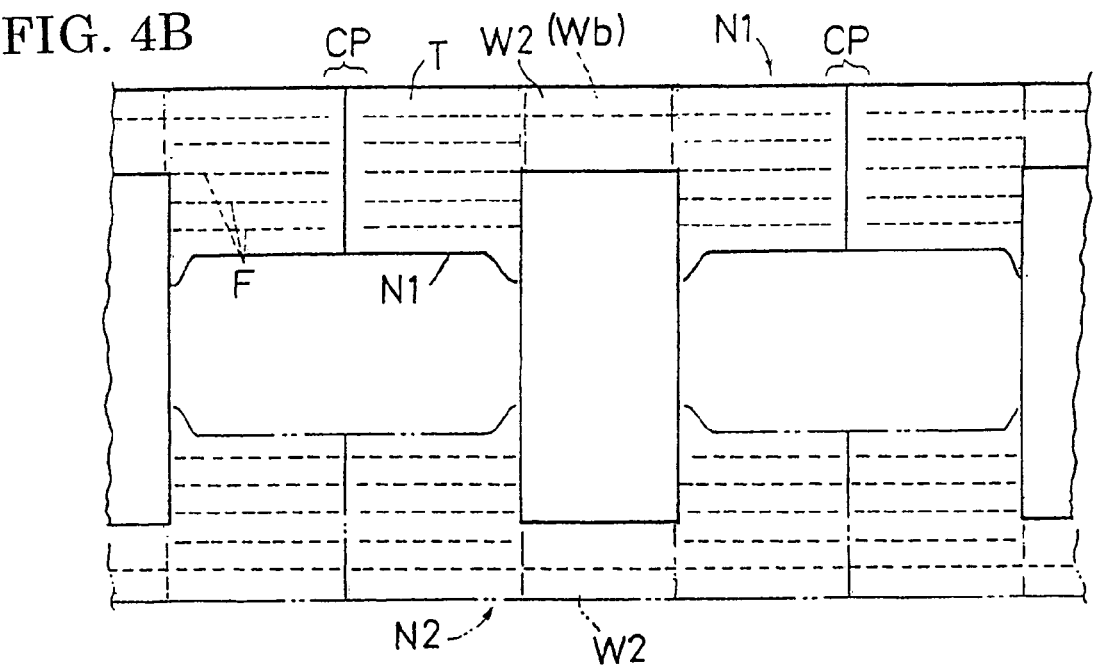
FIG. 4B is a front view showing a wearing article.

A portion represented by a solid line in FIG. 4B shows an example of a disposable diaper produced by the production method of the present invention. In the stack N1, at least a part of an absorber C is fixed at the portion Wb of the stack N1 where the elastic member F is not placed. The other end of the absorber C is connected to another stack N2 represented by a broken line. The absorber C is folded into two, and the portion CP of the stack N1 comes into contact with a corresponding portion of another stack N2, whereby continuous disposable diapers can be produced. Another stack N2 may have the same configuration as that of the stack N1. Furthermore, in the case where the absorber C is folded into two, and the portion CP of the stack N1 comes into contact with the corresponding portion of another stack N2, whereby the stacks N1 and N2 are stretched in a flow direction, even if the elastic member F is placed at the portion CP, the above connection can be conducted.

Figure 12:
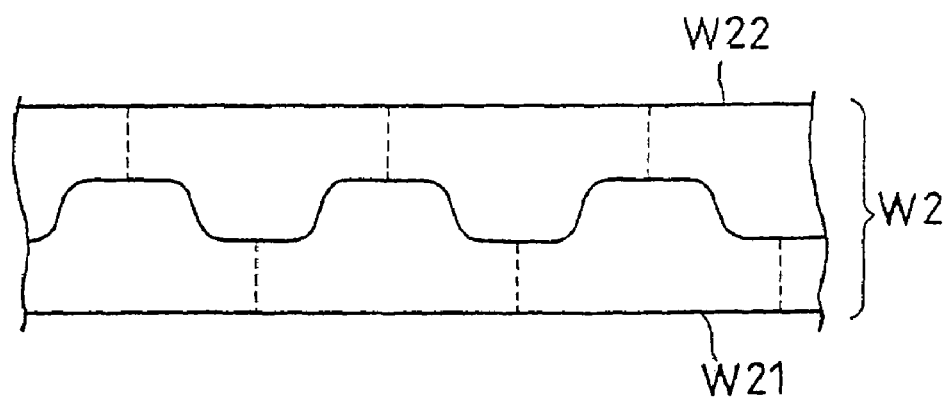
FIG. 12 shows diapers obtained by cutting the elastic member so that a trim is not generated, and shifting the phase of one web thus cut by substantially ½ from the other web.

Furthermore, the following may also be possible: when the elastic member F is cut so that a trim is not generated as shown in FIG. 12, and the phase of one web thus cut is shifted by substantially ½ from the other web, whereby the web W2 shown in FIG. 4B is formed. As a method for shifting a phase, one web may be allowed to pass through a dummy roller to cause a delay from the other web.

Embodiment 2

Figure 6:
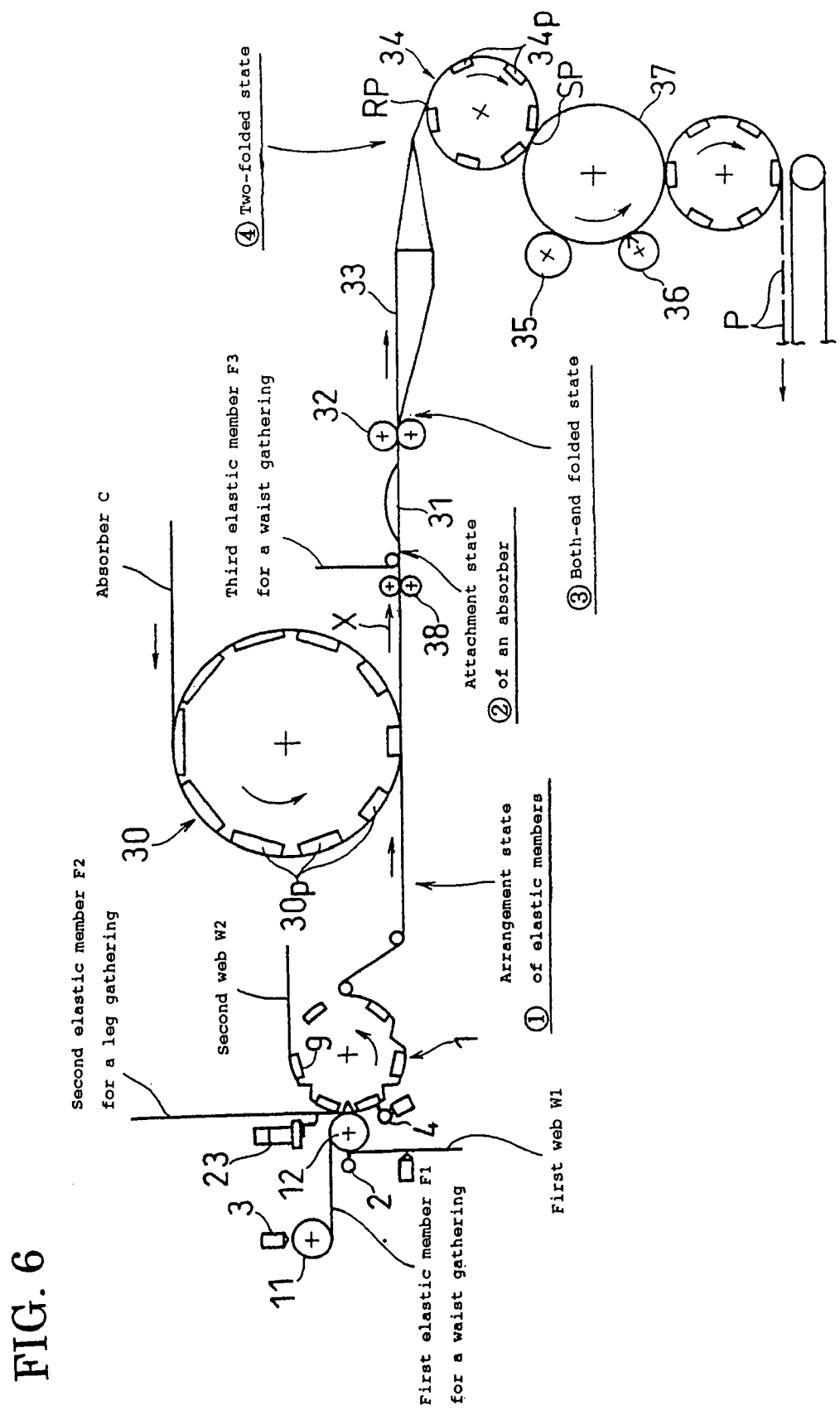
FIG. 6 is a side layout view showing an apparatus for producing a wearing article of Embodiment 2 according to the present invention.
Figure 9A:
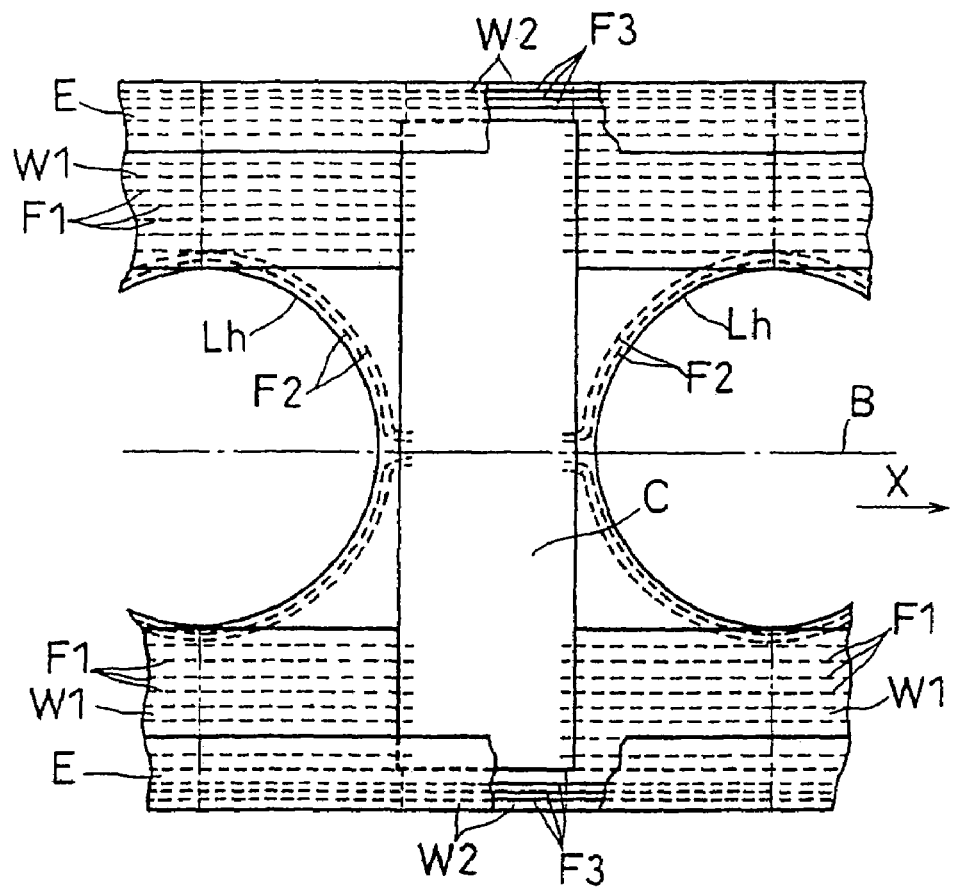
FIG. 9A shows webs whose both edges are bent.

Next, Embodiment 2 will be described. A production apparatus shown in FIG. 6 is capable of placing at least three kinds of elastic members F1 to F3 for a leg gathering on a wearing article, as shown in FIG. 9A.

Figure 7:
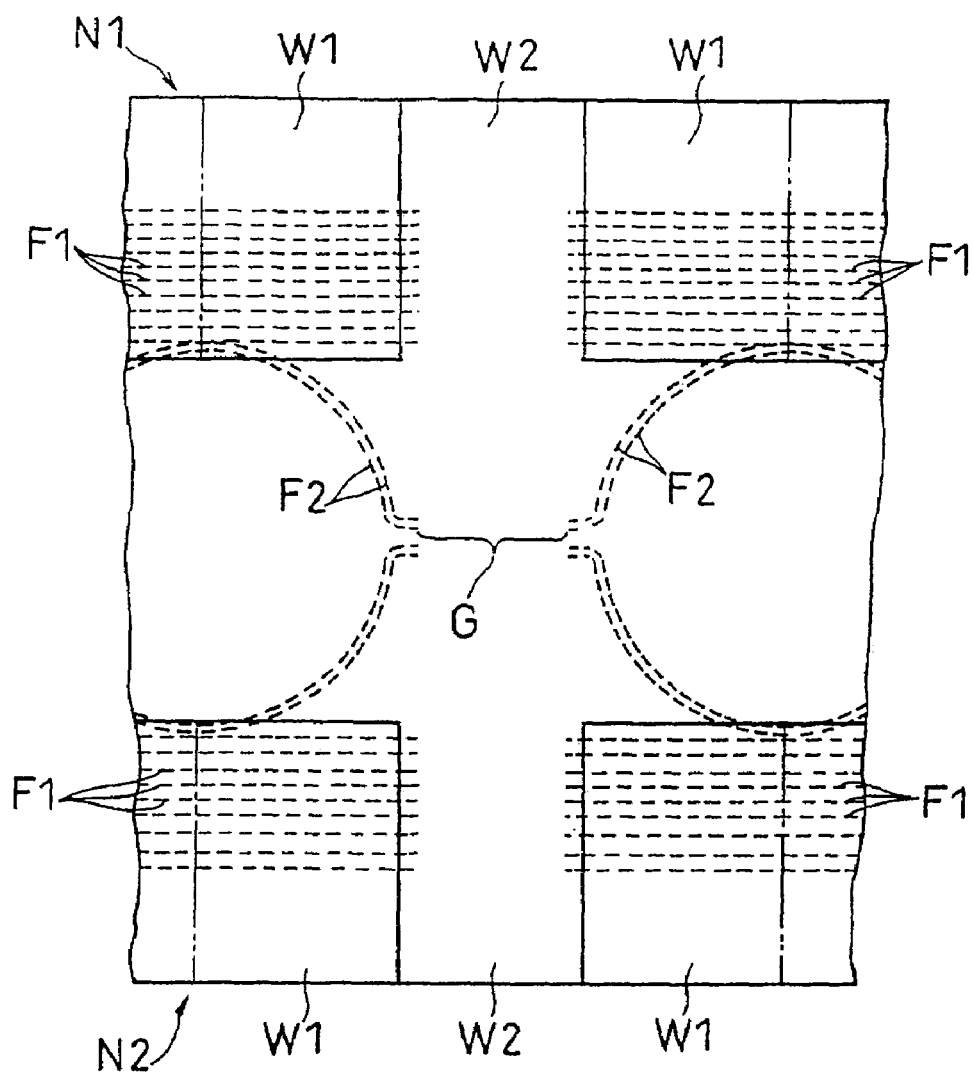
FIG. 7 is a front view showing webs in a state where the elastic member is placed.

(1) Arrangement State of Elastic Members:

First, as shown in FIG. 7, the configuration and operation of the present apparatus for obtaining an arrangement state of elastic members, in which first and second elastic members F1 and F2 are placed on webs W1 and W2, will be briefly described.

The present apparatus includes a first roller 11 for placing a first elastic member 1 for a waist gathering and a guide unit 23 for placing a second elastic member 2 for a leg gathering. The guide unit 23 is capable of arranging the second elastic member F2 for a leg gathering in a curved shape or a linear shape by being reciprocated in the axis direction of a second roller 12 with, for example, a cam or a servo motor. U.S.

patent application Ser. No. 10/095,959 discloses an example of the guide unit 23. The second elastic member F2 may be cut mechanically with scissors, a blade, or the like provided at the roller. FIGS. 11A to 11D show examples of a cutter. The first elastic member F1 may not be a thermoplastic elastic member. In this case, the first elastic member F1 can be cut with scissors, a blade, or the like in the same way as in the second elastic member F2. Furthermore, the first and second elastic members F1 and F2 may be cut with the same scissors, blade, or the like. In the steps until here in Embodiment 2, the other configuration is the same as that of Embodiment 1. Like parts are denoted with like reference numerals, and the detailed description and drawings are omitted here.

After being interposed and fixed between the first and second webs W1 and W2, the first and second elastic members F1 and F2 are cut to be arranged as shown in FIG. 7.

In some disposable wearing articles, an elastic member for a leg gathering is placed on a crotch portion. Therefore, such a portion contrasts to cause an unsatisfactory feeling during wearing. In order to avoid this, the elastic member on the crotch portion is cut so as to shrink, whereby the elastic member on the crotch portion can be made short to some degree. However, it is impossible to completely eliminate the elastic member on the crotch portion, so that an unsatisfactory feeling may still remain.

Figure 10A:
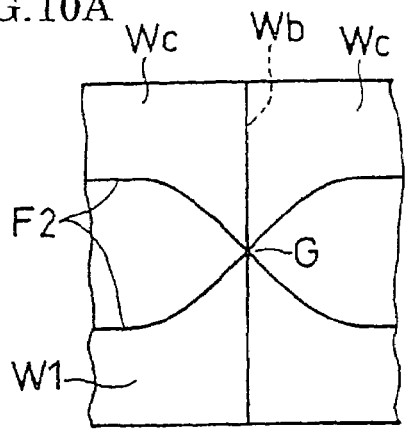
FIGS. 10A to 10F are front views illustrating a method for placing a second elastic member.
Figure 10B:
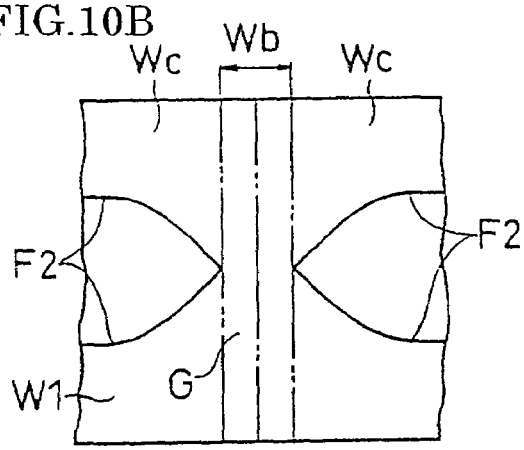
Figure 10C:
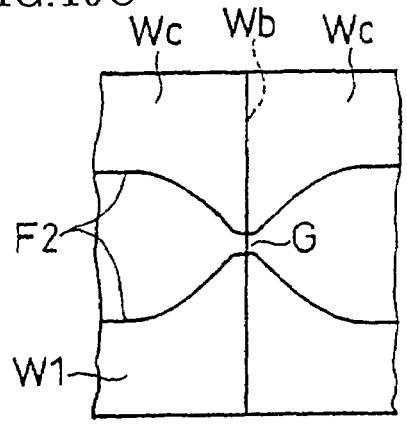
Figure 10D:
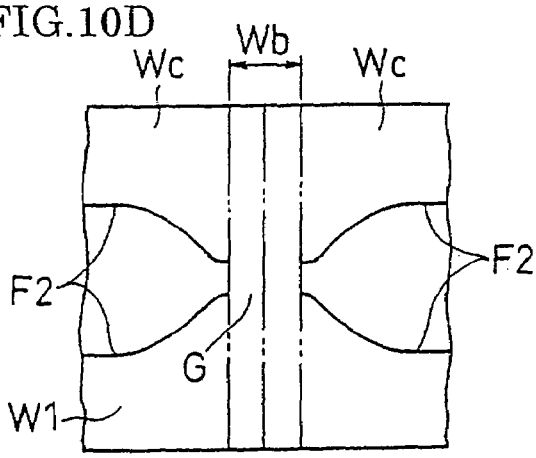
Figure 10E:
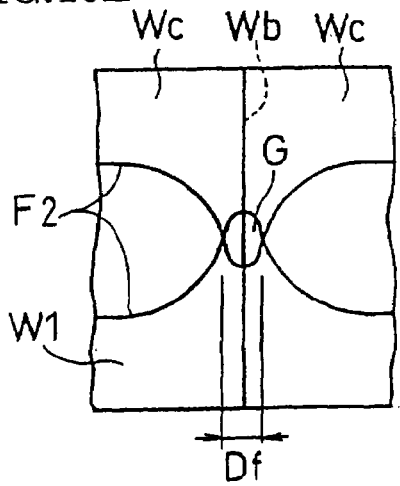

In contrast, when the second elastic member F2 for a leg gathering is placed as shown in FIGS. 10A, 10C, and 10E, the second elastic member F2 can be eliminated from the crotch portion G. FIGS. 10A, 10C, and 10E show the second elastic member F2 interposed between the first web W1 and the second web W2 on adjacent pads 9, wherein a part of the web W2 is interposed between the adjacent pads 9.

For example, as shown in FIGS. 10A and 10c, a folded portion Wb is formed on the crotch portion G of the first web W1, and the second elastic member F2 is placed on non-folded portions Wc. Thereafter, the second elastic member F2 striding across the adjacent pads 9 is cut. As a result, the second elastic member F2 is not placed on the crotch portion G, as shown in FIGS. 10B and 10D.

Figure 10F:
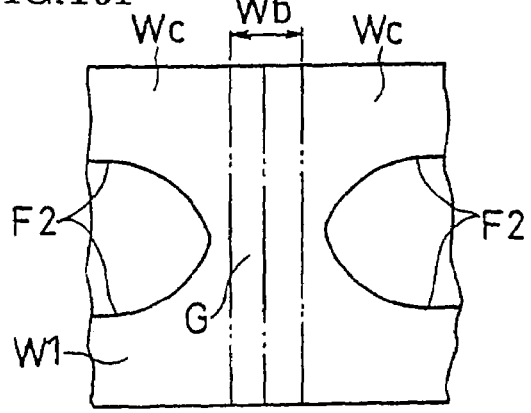

Furthermore, as shown in FIG. 10e, when a non-coated portion Df with no adhesive applied thereto is provided in the non-folded portion Wc adjacent to the vicinity of the folded portion Wb, after the second elastic member F2 is cut, a portion of the second elastic member F2 that is not sufficiently attached to the non-folded portion Wc shrinks (FIG. 10F). Full-circle pants may be produced by such adjustment of an adhesive. Some adhesive may be applied to the non-coated portion Df. In this case, the second elastic member F2 shrinks slowly without being fixed to the non-folded portion Wc, and finally, the second elastic member F2 can be eliminated from the crotch portion G.

The adhesive only needs to be applied to a portion where the second elastic member F2 is placed. As a coating method, an adhesive may be applied in an annual shape to at least one of the first and second webs W1 and W2 with a coater or the like. Furthermore, guns with a plurality of valves are placed in a direction across the first web W1 so that opening/closing of the valve may be controlled by the flow speed of at least one of the first web W1 and the second web W2 and the coating shape. In the case of using such guns, an adhesive can be applied in arbitrary regions partitioned in a matrix.

(2) Attachment State of an Absorber:

An absorber C is arranged and attached to the webs W1 and W2 in the above-mentioned arrangement state of the elastic members by a turn apparatus 30. Thereafter, a third elastic member F3 for a waist gathering is placed to form an attachment state of an absorber as shown in FIG. 8.

The turn apparatus 30 is provided with a plurality of suction pads 30p around a drum (not shown). The suction pads 30p are rotated in an arrow direction while changing the posture of the absorber C by 90° by turning. As the turn apparatus 30, for example, an apparatus as disclosed by International Publication No. WO 01/44086 or U.S. patent application No. US 2002/0103468 may be used.

Figure 8:
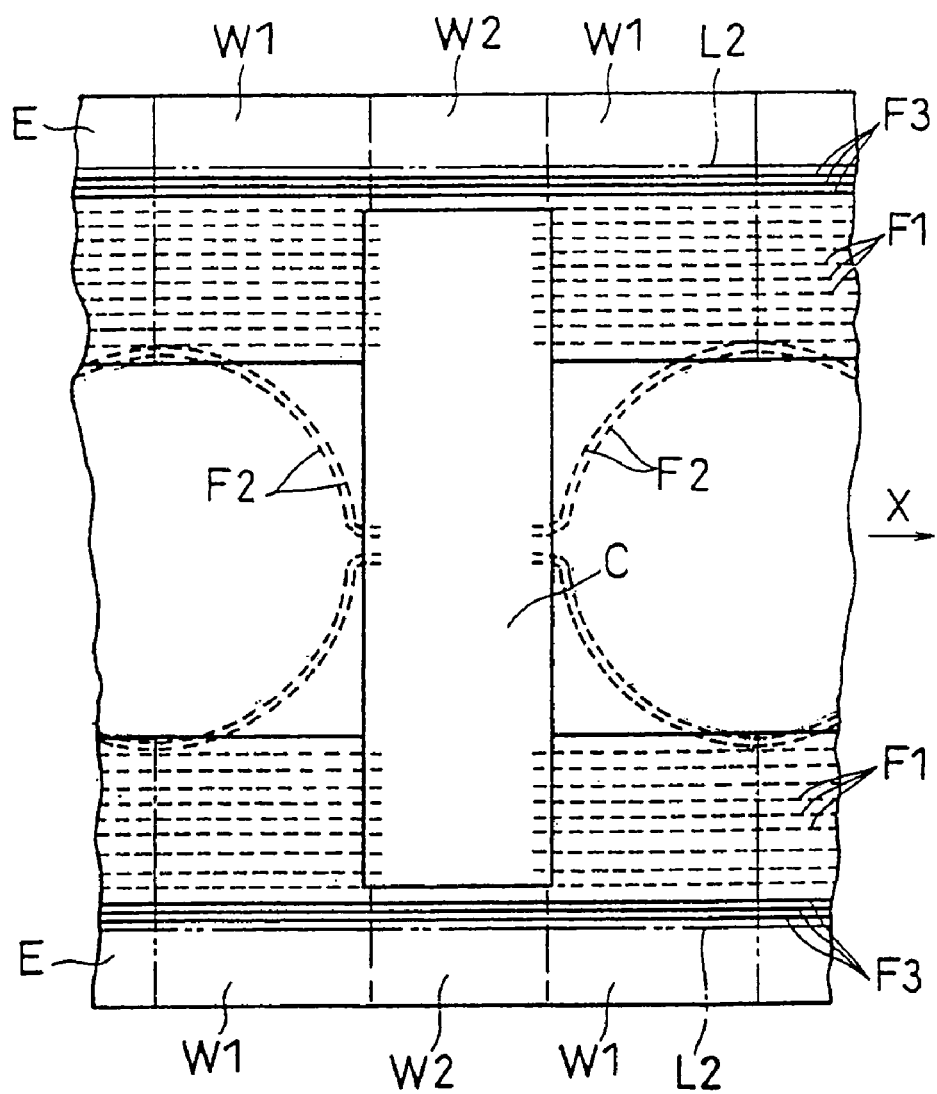
FIG. 8 is a front view showing webs in a state where an absorber is attached.

(3) Both-edge folded state:

Thereafter, the webs W1 and W2 with the absorber attached thereto have their folding portions E on both edges folded inward at a position of two-dot dash lines $L_2$ shown in FIG. 8 by a folding apparatus 31. After both edges of the webs W1 and W2 are folded, a leg hole Lh is cut out with a leg hole cutter 32 (FIG. 6), whereby a both-edge folded state shown in FIG. 9A is formed. The leg hole cutter 32 may be placed upstream from the turn apparatus 30. In such a configuration, it also becomes possible to produce a disposable wearing article in which a part of the absorber C extends out to the leg hole Lh portion.

Figure 9B:
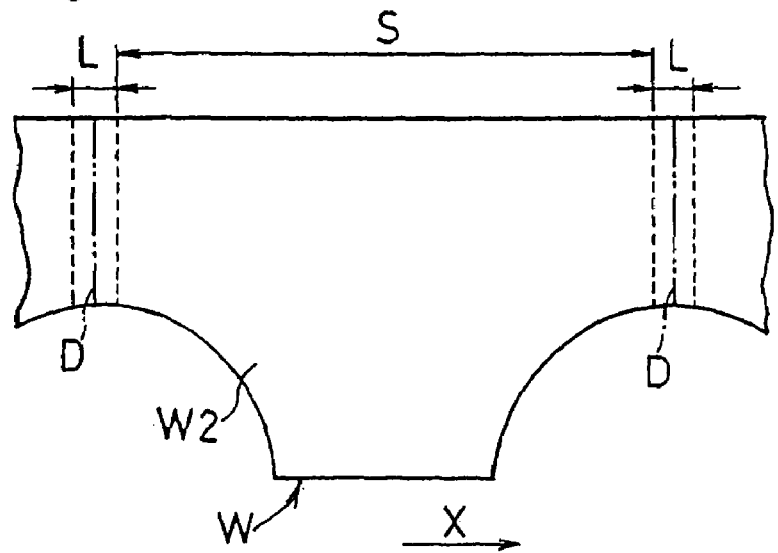
FIG. 9B shows webs folded into two.

(4) Two-folded State:

After folding, the webs W1 and W2 are folded into two at a folding line B by a two-folding apparatus 33, whereby the webs W1 and W2 are folded into two as shown in FIG. 9B. As the two-folding apparatus 33, for example, an apparatus described in U.S. Pat. No. 3,828,367, U.S. Pat. No. 5,711,832, or U.S. patent application Ser. No. 10/147,644 may be used.

Thereafter, the webs W1 and W2 folded into two have both edges L sealed (e.g., heat-sealed or sonic-sealed), as shown in FIG. 9B. Thereafter, a cutting portion D represented by a two-dot dash line is cut to form an individual disposable wearing article, e.g., pants P.

The present apparatus may form pants P from the webs W1 and W2 (hereinafter, referred to as a "stacked web W") folded into two, using a decelerating drum 34, a main drum 37, a seal roller 35, and a cutter roller 36.

Decelerating Drum 34:

As described above, although the web W has an elastic member, the web W is moved in a stretched state so that placement of an absorber at a predetermined position, formation of a leg hole, and other processing can be performed easily. However, in order to seal the web W and cut a seal portion, the position of the edge L only needs to be determined. This is because the state of the other portions of the web W does not influence a sealing step and a cutting step. Furthermore, in the sealing step, it is preferable that a flow speed of the web W is lower so as to obtain a sufficient time for melting a part of the web W and the like. The decelerating drum can decrease the flow speed of the web W so as to obtain a sufficient time for melting the part of the web W and the like. As the decelerating drum 34, an apparatus described in JP 63-317576 A, International Publication No. WO 01/44086, or U.S. Patent Application No. 2002/0103468 may be used.

The decelerating drum 34 is provided with a plurality of pads 34p rotating in a transport direction of the stacked web W around a drum (not shown). The decelerating drum 34 receives at least an edge L at a receiving position RP from the two-folding apparatus 33 placed upstream therefrom, and holds it. The other portions of the web W are positioned between adjacent pads 34p. The edge L is transported to a releasing position SP, and thereafter, the edge L is supplied to the main drum 37 placed downstream therefrom at the releasing position SP. While the pad 34p moves from the receiving position RP to the releasing position SP, the interval between the adjacent pads 34p is changed to be narrow.

The pad 34p is capable of receiving the edge L in a stretched state at the receiving position RP, and keeping holding the edge L shown in FIG. 9B. For example, the edge L may be held by sucking the edge L, pressing the edge L with a hook, or fixing the edge L with a pin placed at the pad 34p. On the other hand, the interval between the adjacent pads 34p, which has been increased at the receiving position RP, is decreased before the releasing position SP, and a shrinking portion S excluding the edge L shrinks in a transport direction X. In order to allow the edge L to be exactly held, the shrinking force of the elastic member positioned at the edge L may be weakened by an embossing roller 38. For example, the embossing roller 38 can cut the elastic member to a predetermined length or change the elastic configuration of the elastic member by using at least one of heat and pressure. As the embossing roller 38, for example, an apparatus described in U.S. Patent Application No. 2002/0103468 may be used. The embossing roller 38 is placed in a region from the rotation apparatus 1 to the two-folding apparatus 33.

Main Drum 37:

The main drum 37 receives the web W in a mixed state where the stretched edge L and the shrinking portion S that has shrunk are present alternately from the decelerating drum 34. The main drum 37 transports the web W in such a mixed state. In order to keep the mixed state, the main drum 37 may be provided with, for example, a plurality of suction holes to suck air through the suction holes so as to suck the web W.

Seal Roller 35:

The seal roller 35 can conduct heat-sealing by heating and pressing the edge L (FIG. 9B) of the web W. More specifically, the web W is pressed by being interposed between the seal roller 35 and the main drum 37, and heated by the seal roller 35. The seal roller 35 may be provided with, for example, a heater so as to heat-seal the edge L. Furthermore, the seal roller 35 may have a horn to conduct sonic-sealing. The web W subjected to the above-mentioned heat-sealing is cut to individual pants P by a cutter roller 36 placed downstream therefrom.

Formation Operation of Pants P:

Next, an operation of forming pants P from the stacked web W will be described. The decelerating drum 34 continuously receives the web W onto each pad 34p under the condition that the web W is stretched in a flow direction. Herein, the pad 34p holds the edge L (FIG. 9B) of the web W in a stretched state.

After receiving the web W, the pad 34p having received the web W has its circumferential velocity decreased, whereby the interval between the adjacent pads 34p becomes narrow. Therefore, a portion S other than the edge L of the web W shown in FIG. 9B shrinks in a transport direction X to form the shrinking portion S. On the other hand, the edge L is held in a stretched state.

Thereafter, the main drum 37 receives the web W from the decelerating drum 34. At this time, the main drum 37 receives the web W in a mixed state where the edge L in a stretched state and the shrinking portion S that has shrunk are present alternately. The main drum 37 transports the web W in a downstream direction while keeping the mixed state. During transportation by the main drum 37, the seal roller 35 presses and heats the edge L of the web W on the main drum 37. Herein, a part of the web W shrinks, so that the transport velocity of the web becomes low. Sealing can be conducted exactly, as the transport velocity of the web W is low.

Thereafter, the web W is cut to individual pieces with a cutter roller 36 to form pants P.

As described above, according to the present invention, after being interposed and fixed between a first web and a second web, an elastic member is cut. Therefore, the stretched elastic member hardly shrinks on the second web, whereby an expected gathering is obtained.

Furthermore, according to the present invention, the elastic member is cut between adjacent first webs. Therefore, the second web and an absorber do not become stiff between the first webs.

Furthermore, a plurality of first webs are placed on a second web under the condition where they are away from each other. Therefore, the first web is not stacked on a portion where a gathering of the elastic member is not formed, so that such a portion becomes thin and allows air to pass there through. As a result, a user wearing such an article is not likely to feel stuffy.

Furthermore, the elastic member is cut between the first webs and at a loose portion of the second web. Therefore, only the elastic member can be cut without damaging the web.

If a pad that makes the second web loose is allowed to transport the second web at a substantially constant velocity during a predetermined period from a time when the pad starts receiving the first web to a time when the pad finishes receiving it, the first web can be transferred to a predetermined position of the second web exactly.

Furthermore, if the elastic member is cut under the condition that the tension stress of the elastic member is increased, the elastic member can be cut easily with infrared rays or the like.

Furthermore, while the web is transported under the condition that an edge (where the web is stretched) and a shrinking portion (where the web shrinks) are present alternately in a transport direction, a heating time for heating the edge becomes long. Therefore, the transport velocity of the web can be increased without impairing the exactness of heat-sealing.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An apparatus for producing a wearing article, comprising:
   means for supplying an elastic member;
   means for stretching the elastic member;
   means for placing the stretched elastic member so that the elastic member spreads across a plurality of first webs divided in a transport direction;
   means for making a part of a second web loose in the transport direction while transporting the second web, thereby forming a loose portion;
   means for placing the first web, on which the elastic member is disposed, on non-loose portion before and after the loose portion of the second web; and means for cutting the elastic member between adjacent first webs of the plurality of first webs.

2. The apparatus for producing a wearing article according to claim 1, wherein, in forming the loose portion, the second web is transported at a substantially constant velocity during a predetermined period by a first pad among a plurality of pads disposed away from each other and having varying movement velocities, and an interval between the first pad and a second pad adjacent to the first pad is decreased to generate the loose portion.

3. The apparatus for producing a wearing article according to claim 1, wherein, in placing the first web, a first pad corresponding to non-loose portion of the second web among the plurality of pads having varying movement velocities is rotated at a substantially constant velocity.

4. The apparatus for producing a wearing article according to claim 1, further comprising means for placing an absorber on a region between the adjacent first webs.

5. The apparatus for producing a wearing article according to claim 1, wherein a material containing, as the elastic member, at least one of thread rubber, flat rubber, mesh-shaped rubber, a film, and a thermoplastic elastic member.

6. The apparatus for producing a wearing article according to claim 1, wherein the means for cutting the elastic member cuts by adding at least heat to the elastic member between the adjacent first webs.

7. The apparatus for producing a wearing article according to claim 6, wherein the means for cutting the elastic member cuts in a state where stress of the elastic member is increased by allowing the adjacent first webs to be away from each other during transportation.

8. The apparatus for producing a wearing article according to claim 1, wherein the means for cutting the elastic member cuts the elastic member between the adjacent first webs with at least one of scissors and an edge.

9. An apparatus for producing a wearing article, comprising:
   a roller means for supplying a plurality of first webs divided in a transport direction at a predetermined position in a state where an elastic member is placed so as to spread across the first webs;
   rotation means including a plurality of pads for rotating the plurality of pads to continuously transport a second web and approach the roller means at the predetermined position; and
   cutter means for cutting the elastic member,
   wherein the rotation means rotates the respective pads of the rotation means so as to have varying circumferential velocities, the respective pads of the rotation means receive the second web at a receiving position upstream from the predetermined position, and after receiving, an interval between the adjacent pads is decreased while the pads are rotated to the predetermined position, whereby a loose portion is formed in the second web,
   the first webs are placed to be stacked on a surface of the second web on a basis of the pads at the predetermined position,
   an interval between the adjacent pads is increased while the respective pads of the rotation means are rotated from the predetermined position to a releasing position downstream from the predetermined position, and
   the cutter means cuts the elastic member in the loose portion while the pads are rotated from the predetermined position to the releasing position.

10. An apparatus for producing a wearing article, comprising:
    means for supplying a first elastic member, a first web, and a second web;
    means for stretching the first elastic member;
    means for cutting the first web to a predetermined length in a transport direction to form cut first webs;
    means for making a part of the second web loose in the transport direction, thereby forming a loose portion;
    means for putting the stretched first elastic member between the cut first webs and the second web to place the cut first webs on non-loose portions before and after the loose portion of the second web; and
    means for cutting the first elastic member above the loose portion.

11. The apparatus for producing a wearing article according to claim 10, further comprising means for guiding a second elastic member for a leg gathering between the cut first webs and the second web.

12. The apparatus for producing a wearing article according to claim 10, wherein, in forming the loose portion, the second web is transported at a substantially constant velocity during a predetermined period by a first pad among a plurality of pads having varying movement velocities, and an interval between the first pad and a second pad adjacent to the first pad is decreased to generate the loose portion.

13. The apparatus for producing a wearing article according to claim 11, wherein, in forming the loose portion, the second web is transported at a substantially constant velocity during a predetermined period by a first pad among a plurality of pads having varying movement velocities, and an interval between the first pad and a second pad adjacent to the first pad is decreased to generate the loose portion.

14. The apparatus for producing a wearing article according to claim 10, wherein, in putting the stretched first elastic member, a first pad corresponding to non-loose portion of the second web among the plurality of pads having varying movement velocities is rotated at a substantially constant velocity.

15. The apparatus for producing a wearing article according to claim 11, wherein, in putting the stretched first elastic member, a first pad corresponding to non-loose portion of the second web among the plurality of pads having varying movement velocities is rotated at a substantially constant velocity.

16. The apparatus for producing a wearing article according to claim 10, further comprising means for placing a side of an absorber on a region between the adjacent first webs.

17. The apparatus for producing a wearing article according to claim 11, further comprising means for placing a side of an absorber on a region between the adjacent first webs.

18. The apparatus for producing a wearing article according to claim 10, wherein a material containing, as the first elastic member, at least one of thread rubber, flat rubber, mesh-shaped rubber, a film, and a thermoplastic elastic member.

19. The apparatus for producing a wearing article according to claim 11, wherein a material containing, as the second elastic member, at least one of thread rubber, flat rubber, mesh-shaped rubber, a film, and a thermoplastic elastic member.

20. The apparatus for producing a wearing article according to claim 10, wherein the means for cutting the first elastic member cuts by adding heat to the first elastic member between the adjacent first webs.

21. The apparatus for producing a wearing article according to claim 11, wherein the first and second elastic members are cut by adding heat to the first and second elastic member between the adjacent first webs.

22. The apparatus for producing a wearing article according to claim 10, wherein the first elastic member is cut in a state where stress of the first elastic member is increased by allowing the adjacent first webs to be away from each other during transportation.

23. The apparatus for producing a wearing article according to claim 11, wherein the first and second elastic members are cut in a state where stress of the first and second elastic members are increased by allowing the adjacent first webs to be away from each other during transportation.

24. The apparatus for producing a wearing article according to claim 10, wherein the first elastic member between the adjacent first webs is cut with at least one of scissors and an edge.

25. The apparatus for producing a wearing article according to claim 11, wherein the first and second elastic member between the adjacent first webs is cut with at least one of scissors and an edge.

* * * * *